United States Patent [19]

Boltze et al.

[11] Patent Number: 4,513,004

[45] Date of Patent: Apr. 23, 1985

[54] INDOLE DERIVATIVES, PROCESSES FOR THEIR PREPARATION, AND THEIR USE AS MEDICAMENTS

[75] Inventors: Karl-Heinz Boltze, Borod; Harald Horstmann, Wuppertal, both of Fed. Rep. of Germany

[73] Assignee: Troponwerke GmbH & Co. KG, Cologne, Fed. Rep. of Germany

[21] Appl. No.: 463,370

[22] Filed: Feb. 3, 1983

[30] Foreign Application Priority Data

Feb. 26, 1982 [DE] Fed. Rep. of Germany ....... 3206885

[51] Int. Cl.$^3$ ................. C07D 405/12; A61K 31/405
[52] U.S. Cl. .................................... 514/414; 548/465; 548/467; 548/238
[58] Field of Search ................. 548/465, 467; 424/274

[56] References Cited

U.S. PATENT DOCUMENTS 3,161,654 12/1964 Shen .................................... 424/274
4,391,814 7/1983 Vorbrüggen ....................... 548/238

FOREIGN PATENT DOCUMENTS 2735537 2/1979 Fed. Rep. of Germany .
2740852 3/1979 Fed. Rep. of Germany .
2853824 7/1980 Fed. Rep. of Germany .
1417080 12/1975 United Kingdom .

OTHER PUBLICATIONS

Alter, Chem. Abstracts vol. 87: 39279u (1977).
Alter, Chem. Abstracts vol. 87: 39280n (1977).
Boltze et al., *Arzneim-Forsch*, 30 (8A), (1980), pp. 1314–1325.
Dell et al., *Arzneim-Forsch*, 30 (8A), (1980), 1362–1370.

*Primary Examiner*—Donald G. Daus
*Assistant Examiner*—William A. Teoli, Jr.
*Attorney, Agent, or Firm*—Sprung, Horn, Kramer & Woods

[57] ABSTRACT

The invention relates to indole derivatives identified herein by Formula (I) and a method for their preparation.

Also included in the invention are compositions containing said indoles and methods for their use as antiphlogistic agents.

6 Claims, No Drawings

INDOLE DERIVATIVES, PROCESSES FOR THEIR PREPARATION, AND THEIR USE AS MEDICAMENTS

The present invention relates to new indole derivatives, processes for their preparation, and their uses as medicaments.

It has already been disclosed that indole derivatives may be used as antiphlogistics in medicine. The following may be mentioned as examples: cinametacin [INN; 1-cinnamoyl-5-methoxy-2-methyl-3-indole-acetic acid] and indometacin [INN; 1-(4-chlorobenzoyl)-5-methoxy-2-methyl-3-indoleacetic acid]. Both compounds have a strong acid functional group, so that side-effects are inevitable. Thus, J. Solinca (see Arzneimittelforschung [Drug Research] 21, No. 11A (1971), page 1834) has observed very frequently neurosensitive disease such as headache, dizziness and difficulities in concentration, as relatively slight side-effects, and also frequently found indigestion with loss of appetite, nausea, stomach ache and diarrhoea, and finally a few severe cases of intestinal bleeding and gastric ulcers, and in some cases symptoms of neurological disturbance. G. Morandi and U. Serni (see Arzneimittelforschung [Drug Research] 21, No. 11a (1971), page 1834) have found that, owing to the side-effects, the therapy had to be discontinued in the case of almost one in ten patients.

The invention relates to new indole derivatives of the formula (I)

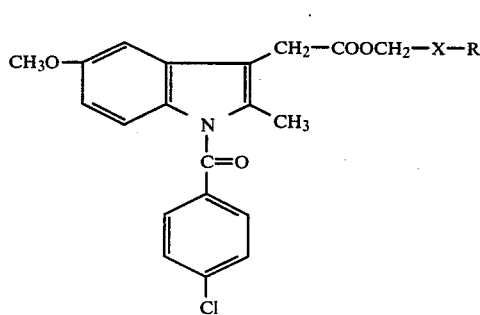

in which

X represents —COO— or —CONH— and

R represents a tetrahydrofuran-2-yl-, a tetrahydropyran-2-yl, an alkoxybenzyl- or a straight or branched alkyl group which can optionally be substituted by a hydroxyl group, or X-R together form an oxazoline ring which can be substituted by alkyl groups, and their pharmaceutically acceptable salts.

The new indole derivatives of the general formula (I) have advantageous effects in the case of diseases caused by inflammation and in the case of diseases of the rheumatic form. Furthermore, they may be advantageously employed as starting compounds for the preparation of acemetacin which is free of deschloracemetacin. This use is preferred according to the invention. When used for this purpose, the protective groups can be readily split off, if necessary using cleavage reagents, and acemetacin can be obtained in high yield and purity.

The present invention furthermore relates to a process for the preparation of indole derivatives of the formula (I), which is characterised in that salts of the indolecarboxylic acid of the formula (II)

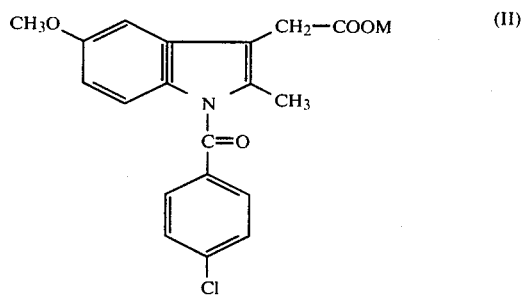

in which M represents ammonia, an alkali metal or corresponding stoichiometric amount of alkaline earth metal, preferably potassium or sodium, and compounds of the formula (III)

Hal—CH₂—X—R (III)

in which

Hal represents chlorine, bromine or iodine, preferably bromine, and

X and R have the meaning given in Formula (I) supra, are reacted in the presence of an inert organic solvent, or a mixture of organic solvent with water, in a temperature range from −30° to +70° C.

If the potassium salt of indolecarboxylic acid is used as a representative compound of the formula (II), and compounds of the formula (III) are used as starting materials, the course of the reaction can be represented by the following equation:

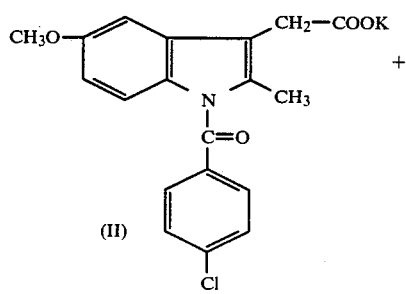

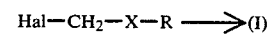

Hal—CH₂—X—R ⟶ (I)

(III)

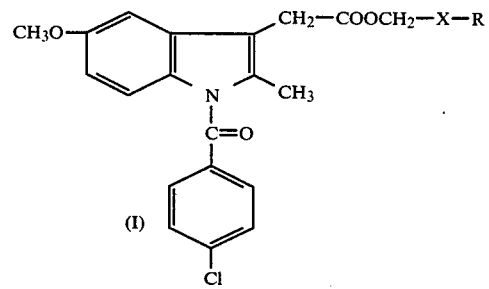

The compounds of the formula (II) and (III) which are used as starting materials are known, or are prepared by known processes. Preferably, the following substances are employed as compounds of the formula (III): tetrahydrofuran-2-yl-2-bromoacetate, tetrahydropyran-2-yl-2-bromoacetate, 4-methoxybenzyl-2-bromoacetate, N-(1-hydroxy-2-methylprop-2-yl)-2-bromoacetamide and 4,4-dimethyl-2-oxazolin-2-yl-methyl bromide.

The reaction is advantageously carried out in the presence of diluents. Suitable diluents are in general all inert solvents, preferably inert organic solvents. These preferably include, again, polar and aprotic solvents, such as, for example, chloroform, dichloromethane and dioxane. Tetrahydrofuran, dimethylformamide and hexamethylphosphoric acid triamide are particularly preferably employed. The temperatures can be varied within a relatively wide range, and the reaction is carried out in general at temperatures between approximately $-30°$ and $+70°$ C. The reaction is preferably carried out at between 0° and 40° C., particularly preferably at room temperature, that is to say between approximately 15° and 25° C.

The reaction is preferably carried out under atmospheric pressure.

In carrying out the process according to the invention, the reactants (II) and (III) are advantageously employed in molar amounts. Working-up is carried out in general by diluting the reaction solution with a suitable water-immiscible solvent, washing out the water-soluble parts, filtering the organic phase and chromatographing it over $SiO_2$. The new indole derivatives according to the invention, which can also be referred to as acemetacin derivatives, can, if required, be readily converted into acemetacin by means of cleavage reagents.

Particularly important are the compounds below, of which the pyranyl ester compound is preferred:

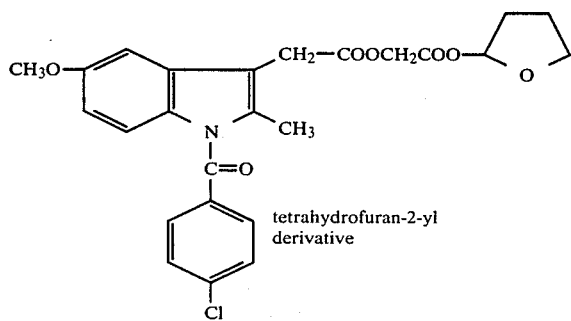

tetrahydrofuran-2-yl derivative

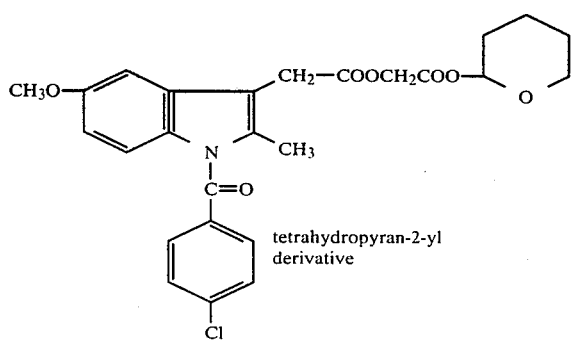

tetrahydropyran-2-yl derivative

The new active compounds have powerful antiinflammatory effects. Thus, in the case of the known pharmacological model of inflammation, the kaolin edema of the rats' paw (see Kemper, Z.ges.exp.Med. 131, 407 (1959), results were achieved which correspond to, and in some cases even surpass, those of the inflammation-inhibitors used in medicine. Even in respect of the increase in the sulphhydryl group activity of serum proteins, which represents a measure of the activity of antiphlogistics (see D. A. Gerber et al., Biochem. Pharmacol. 16, 115 (1967), the majority of the compounds according to the invention were substantially superior to flufenaminic acid which was used as a comparative substance. In combating diseases of the rheumatic form, the compounds according to the invention therefore show promise in enriching medicine.

The present invention includes pharmaceutical formulations which, in addition to non-toxic, inert, pharmaceutically suitable excipients, contain one or more active compounds according to the invention, or which consist of one or more active compounds according to the invention, as well as processes for the preparation of these formulations.

By non-toxic, inert, pharmaceutically suitable excipients there are to be understood solid, semi-solid or liquid diluents, fillers and formulation auxiliaries of every kind. Tablets, dragees, capsules, pills, granules, suppositories, solutions, suspensions and emulsions may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium bicarbonate, (e) solution retarders, for example paraffin, and (f) resorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethylene glycols, or mixtures of the compounds listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients can also be in a micro-encapsulated form.

Suppositories can contain, in addition to the active compound or compounds, the customary water-soluble or water-soluble excipients, for example polyethylene glycols, fats, for example cacao fat, and higher esters (for example $C_{14}$-alcohol with $C_{16}$-fatty acid), or mixtures of these substances.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerol-formal, tetrahydrofurfuryl alcohol, polyethylene glycols and fatty acid esters of sorbitane, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol and sorbitane esters, micro-crystalline cellulose, aluminium metahydroxide, bentonite, agar-agar and traga-canth, or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95% by weight of the total mixture.

The abovementioned pharmaceutical formulations can also contain other pharmaceutically active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in medicine, for the alleviation and/or cure of the abovementioned diseases.

The active compounds or the pharmaceutical formulations can be administered locally, orally, parenterally, intraperitoneally and/or rectally, preferably orally.

In general, it has proved advantageous in medicine, to applicate the active compound or compounds according to the invention in total amounts of about 0.1 to about 200, preferably 0.5 to 10, particularly preferably 0.8–3, such as 1.2 or 1.7 mg/kg of body weight every 24 hours, optionally in the form of several individual applications, in order to achieve the desired results. An individual does contains the active compound or compounds according to the invention preferably in amounts of about 0.1 to about 70, in particular 0,1. to 2.0 particularly preferably 0.2–0.5 mg/kg of body weight. However, it may be necessary to deviate from the dosages mentioned, and in particular to do so as a function of the species and the body weight of the object to be treated, and the nature and severity of the disease. The new acemetacin derivatives are characterized on the basis of their chemical name and their formula in the particular example in each case. In the examples, only the radical representing -X-R in each case is given, corresponding to the formula (I).

EXAMPLES

EXAMPLE 1

Preparation of tetrahydrofuran-2-yl-[1-(4-chlorobenzoyl)-5-methoxy-2-methylindole-3acetoxy]-acetate

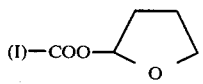

Tetrahydrofuran-2-yl-2-bromoacetate

The glycolic acid derivative is obtained by reacting 6.95 g (0.05 mol) of bromoacetic acid and 2.80 g (0.4 mol) of 2,3-dihydrofuran at room temperature in the absence of moisture, and stirring the mixture after 5 hours (bromoacetic acid is converted quantitatively). This reaction solution was employed in the following synthesis step, without isolation. The glycolic acid derivative has the formula:

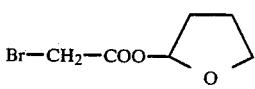

Acemetacin derivative 3.58 g (0.01 mol) of 1-(4-chlorobenzoyl)-5-methoxy-2-methylindole-3-acetic acid are dissolved in 20 ml of absolute dimethylformamide, 0.7 g (0.0051 mol) of dried and powdered potassium carbonate are added, and the potassium salt is allowed to form, while stirring at 55° C.

7 g of the above reaction solution (=2.1 g) (0.01 mol) of tetrahydrofuran-2-yl-2-bromoacetate are then added dropwise to the clear solution of the potassium salt at room temperature. After 2 hours, the reaction is complete (pH approximately 4).

The reaction mixture is cooled to 0° C., 200 ml of cold ethyl acetate are added, and the mixture is extracted by shaking successively with ice-cold, semi-concentrated potassium bicarbonate solution and ice-cold, greatly diluted potassium bicarbonate solution, and 3 times with ice-water. After drying over $Na_2SO_4/K_2CO_3$, the excess 2,3-dihydrofuran and the solvent are removed at 10° C. and 40 mm Hg in a rotary evaporator, and 6.8 g of yellow oil are obtained as the residue.

The oil begins to crystallise after 2 days in a deep freeze in the absence of moisture (soda lime tube). To complete the crystallisation, 4 ml of carbon tetrachloride (dried over $K_2CO_3$) are stirred in thoroughly, and the mixture is kept cold (freezer).

The crystals, which have been filtered off under suction, are washed with a small amount of $CCl_4$ and dried over KOH/paraffin chips in a desiccator. Yield: 69.6% of theory; m.p: 86°–88° C.

Preparation of 1-(4-chlorobenzoyl)-5-methoxy-2-methylindole-3-acetoxyacetic acid-acemetacin Splitting off the protective group of the acemetacin derivative according to the invention The tetrahydrofuranyl ester (3.3 g) prepared in the above experiment is dissolved in 30 ml of glacial acetic acid and the solution is heated at 40°–50° C. for 30 minutes. During this process, the protective group is split off quantitatively. After the glacial acetic acid has been distilled off, the residue is crystallised from carbon tetrachloride. The crystals, which have been filtered off under suction, are dried over KOH in a desiccator.

10 ml of semi-concentrated potassium bicarbonate solution and 15 ml of tetrahydrofuran are added to the mother liquor which has been freed from solvent, and the mixture is stirred thoroughly and extracted with 3 times 20 ml of ether. The alkaline phase is acidified and extracted with ethyl acetate, and the organic phase is washed neutral. After the organic phase has been dried over Na$_2$SO$_4$, it is concentrated, and the residue is crystallised from carbon tetrachloride. Total yield: 3.5 g=84.2% of theory.

EXAMPLE 2

Preparation of tetrahydropyran-2-y-[1-(4-chorobenzoyl) 5-methylindole-3-acetoxy]-acetate

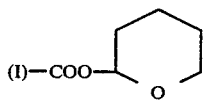

Tetrahydropyran-2-yl-2-bromoacetate

The glycolic acid derivative is obtained by reacting 6.95 g (0.05 mol) of bromoacetic acid and 33.6 g (0.4 mol) of 3,4dihydro-2H-pyran at room temperature in the absence of moisture and under a protective atmosphere of N$_2$, and stirring the mixture for 17 hours (quantitative conversion of bromoacetic acid according to thin-layer chromatography and NMR). This reaction solution is employed in the following synthesis step, without isolation. The glycolic acid derivative has the formula:

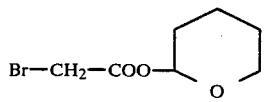

Acemetacin derivative 3.58 g (0.01 mol) of 1-(4-chlorobenzoyl)-5-methoxy-2-methylindole-3acetic acid are dissolved in 20 ml of absolute dimethylformamide, 0.7 g (0.0051) of dried and powdered potassium carbonate is added, and the potassium salt is allowed to form, while stirring for 6 hours at 55°C.

8.1 g of the above reaction solution (approximately 0.01 mol) of tetrahydropyran-2-yl-2-bromoacetate are then added dropwise in the course of 10 minutes to the clear solution of potassium salt, at room temperature. After 2 hours, the reaction is complete (pH 6).

100 ml of ethyl acetate are added to the reaction mixture, and the mixture is extracted by shaking successively with semi-concentrated potassium bicarbonate solution and 4 times with more dilute potassium bicarbonate solution. After drying the solution over Na$_2$SO$_4$/K$_2$CO$_3$, it is filtered, and the solvent is removed at 20° C. and 60 mm Hg in a rotary evaporator. The excess 3,4-dihydro-2H-pyrane is then distilled off at 20° C. and 20 mm Hg.

5.8.g of yellow oil remain.

The crystallisation of the oil begins, in the presence of seed crystals and in the absence of moisture (soda lime tube), in a deep freeze. To complete the crystallisation, 4 ml of carbon tetrachloride (dried over K$_2$CO$_3$) are stirred in thoroughly, and the mixture is kept cold (freezer).

The crystals, which have been filtered off under suction, are washed with a small amount of CCl$_4$ and dried in a desiccator (paraffin/KOH).

The oil obtained from the mother liquor crystallises through completely only after 25 ml of petroleum ether have been added and the mixture has been left to stand for 2 weeks at −15° C.

Total yield: 4.6 g=92.0% of theory.

Preparation of acemetacin

Splitting off the protective group of the acemetacin derivative according to the invention The tetrahydropyranyl ester prepared in the above experiment (4.6g) is dissolved in 30 ml of toluene, 5 mg of p-toluenesulphonic acid are added, and the mixture is stirred for 1 hour at room temperature. The brown reaction solution is freed from toluene and the resulting 3,4-dihydro-2H-pyran at 30° C. in a rotary evaporator; further toluene which has been added is removed in the same manner.

10 ml of water and seed crystals are added to the residue which is dissolved in 30 ml of acetone at 30° C., and 10 ml of water are then again added dropwise in the course of 1 hour, while stirring. The substance does not crystallise through readily.

After the product has been filtered off under suction and washed twice with carbon tetrachloride, an almost colourless substance is obtained. The mother liquor, freed from solvent, leaves a residue which, when recrystallised from carbon tetrachloride, gives a further 2.9 g of product.

Total yield: 3.9 g=93.8% of theory.

EXAMPLE 3

Preparation of 4-methoxybenzyl-[1-(4-chlorobenzoyl)-5-methoxy-2-methylindole-3-acetoxy]-acetate

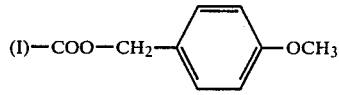

4-Methoxybenzyl 2-bromoacetate 20.2 g (0.1 mol) of bromoacetyl bromide are dissolved in 100 ml of toluene, this solution is cooled to −10° C. (CaCl$_2$ tube) and 8.7 g (0.11 mol) of pyridine are added dropwise at −10° C. Thereafter, 13.8 g (0.1 mol) of 4-methoxybenzyl alcohol, dissolved in 20 ml of toluene are added dropwise to this mixture in the course of 20 minutes at −10° C., and the mixture is allowed to react for 1 hour at this temperature.

The reaction mixture, which has been warmed to room temperature, is extracted by shaking 4 times with water, dried over Na$_2$SO$_4$, freed from solvent in a rotary evaporator, and degassed at 10$^{-2}$ mm Hg and 40° C.

Residue: 23.9 g=92.3% of theory; a brown oil, which is employed without further purification in the following synthesis step.

Acemetacin derivative 7.16 g (0.02 mol) of 1-(4-chlorobenzoyl)-5-methoxy-2-methylindole-3-acetic acid are dissolved in 40 ml of absolute dimethylformamide, 1.38 g of dried and powdered potassium carbonate are added, and the potassium salt is allowed to form, while stirring at 55° C., until a clear, yellow solution has formed after 5 hours.

5.18 g (6.02 mols) of 4-methoxybenzyl 2-bromoacetate are added at room temperature, and the mixture is allowed to react for 3 hours (pH: 6 to 7). 200 ml of ethyl acetate are added to the reaction mixture, and the mixture is extracted 4 times by shaking with 200 ml of water and then twice by shaking with semi-concentrated potassium bicarbonate solution, and is washed neutral with water. After the organic phase has been dried over Na$_2$SO$_4$ and filtered, and the solvent has been evaporated off in a rotary evaporator, an oily residue remains, which gives, from ether/diisopropyl ether, colourless crystals in a yield of 9.4 g=87.8% of theory; m.p.: 88°–90° C.

Preparation of acemetacin

Splitting of the protective group of acemetacin derivative according to the invention The 4-methoxybenzyl ester (5.35 g=0.01 mol) prepared as described above is dissolved in 5.4 g (0.05 mol) of anisole, and 0.73 g (0.02 mol) of glacial acetic acid/HCl (75.9 mg of HCl/ml) is added while stirring and in the absence of moisture. After a reaction time of 5 hours, the conversion is quantitative.

1.8 g (0.023 mol) of ammonium acetate are added to the reaction mixture, the mixture is stirred for 10 minutes, 20 ml of water are added, and stirring is continued for a further 10 minutes. Thereafter, the mixture is extracted with 40 ml of toluene, the organic phase is washed neutral and dried over Na$_2$SO$_4$, and the solvent is distilled off. The residue is stirred throughly with 200 ml of petroleum ether. Crystals are formed, and are filtered off under suction, washed with petroleum ether and dried. The substance is purified by dissolving it in methylene chloride, adding 80 ml of carbon tetrachloride and distilling off the methylene chloride at 70° C. Acemetacin crystallises at room temperature.

Recrystallisation from toluene gave the pure substance in a yield of 2.8 g=67.3% of theory, with a melting point of 150°–151° C.

EXAMPLE 4

Preparation of N-(1-hydroxy-2-methylprop-2-yl)-[1-4-chlorobenzoyl)-5-methoxy-2-methylindole-3-acetoxy]-acetamide

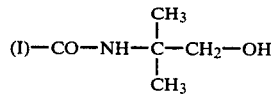

N-(1-Hydroxy-2-methylprop-2-yl)-2-bromoacetamide 35.6 g (0.4 mol) of 1-hydroxy-2-methyl-2-aminopropane are dissolved in 100 ml of absolute methylene chloride, the solution is cooled to 0° C., and 40.4 g (0.2 mol) of bromoacetyl bromide, dissolved in 100 ml of methylene chloride, are added dropwise to this solution in the course of 3 hours 50 minutes, in the absence of moisture and while maintaining the temperature of 0° C. The mixture is allowed to react further for 2 hours at room temperature. The 1-hydroxy-2-methyl-2-aminopropane hydrobromide is filtered off under suction and washed with methylene chloride. The plate yellow oil obtained from the filtrate by evaporating off the solvent is chromatographed over silica gel, using ethylene chloride/isopropanol (95:5; 9:1; 4:1).

Yield: 17.3 g=41.2% of theory; m.p.: 61–63° C.

Acemetacin derivative 17.9 g (0.05mol) of 1-(4-chlorobenzoyl)-5-methoxy-2-methylindole-3-acetic acid are dissolved in 100 ml of absolute dimethylformamide, and, after the addition of 3.7 g (0.027 mol) of powdered potassium carbonate, is converted into the potassium salt after 7 hours at 60° C. 11.3 g (0.054mol) of the N-(1-hydroxy-2-methylprop-2-yl)-2-bromoacetamide obtained as described above are added at room temperature, and the reaction is carried out for 3 hours at 45° C.

The oily residue obtained after the solvent has been distilled off is dissolved in 200 ml of ethyl acetate, and the solution is freed from unreacted starting acetic acid derivative by extracting it 3 times by shaking with semi-concentrated potassium carbonate solution, and is washed neutral with water. The organic phase, after it has been dried (Na$_2$SO$_4$) and filtered and the solvent has been evaporated, leaves a residue which is recrystallised from ether/diisopropyl ether. The residue from the mother liquor is chromatographed over silica gel using cyclohexane/ethyl acetate (2:1).

Total yield: 19.4 g=79.7% of theory, m.p.: 107°–109° C.

Preparation of acemetacin

Splitting off the protective group with dinitrogen tetroxide (a) 3.4 g of dinitrogen tetroxide from a bomb are condensed, in the absence of moisture (Siccopent tube), in a cold trap with a narrow syphon tube, and are diluted to 12 ml with cold absolute tetrahydrofuran (blue solution).

2.4 g (0.005 mol) of the acemetacin derivative are dissolved in 5 ml of flacial acetic acid, 5 ml of absolute dioxane and 1.64 g (0.02 mol) of sodium acetate are added, and the mixture is cooled to 0° C. while stirring. Thereafter, 3.3 ml of the solution a) are added dropwise at 0° C., and the mixture is allowed to react for 2 hours at this temperature (quantitative conversion of the acemetacin derivative).

The reaction mixture is poured onto ice and extracted with cold ether. The ether phase is washed thoroughly with ice-cold water, ice-cold potassium bicarbonate solution and ice-water in succession, dried over MgSO$_4$, filtered, and concentrated to 80 ml at 0° C. in a rotary evaporator. 0.7 g (0.005 mol) of potassium carbonate (finely powdered) is then added, and the mixture is brought to reaction for 3 hours at 0° C., while stirring and in the absence of moisture. The quantity of gas formed is collected in a gas burette (at 0° C.=165 ml; theory: 224 ml). When the mixture stands overnight at room temperature, substantial evolution of gas no longer takes place; however, a substance was precipitated, from which 700 mg of acemetacin were obtained after the ethereal solution had been decanted, the precipitate acidified with acetic acid and the mixture extracted with ethyl acetate.

From the alkaline-aqueous mother liquor of the above ether extraction, a further 200 mg, mainly acemetacin, are obtained by acidification and extraction.

These 900 mg are then chromatographed over silica gel using cyclohexane/ethyl acetate/glacial acetic acid (10:10:1).

Example 5

Preparation of (4,4-dimethyl-2-oxazolin-2-yl)-methyl 1-(4-chlorobenzoyl)-5-methoxy-2-methylindoleacetate

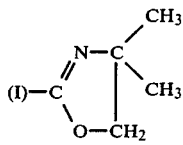

4,4-Dimethyl-2-oxazolin-2-yl-methyl bromide 2.1 g (0.01 mol) of

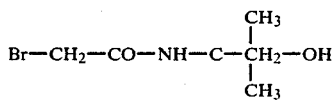

are initially introduced, in the absence of moisture (CaCl$_2$ tube), and 3.5 g (0.03 mol) of thionyl chloride, dissolved in 5 ml of CH$_2$Cl$_2$, are added dropwise at room temperature, while stirring (increase in temperature to 26° C.) Thereafter, the mixture is heated at 40° C. for 2 hours and then allowed to cool to room temperature, and 25 ml of ether are added, while stirring, a yellow oil separating out. This is separated off and again stirred thoroughly with 25 ml of ether. 25 ml of ether are again poured over the oil which is once again isolated, the mixture is cooled to −10° C., and 5 ml of cold 20% strength NaOH are added, while stirring. After the ether phase has been separated off and the aqueous phase has again been extracted with ether, the combined ether phases are extracted by shaking with NaCl solution, dried over Na$_2$SO$_4$, filtered, and freed from solvent in a rotary evaporator.

Residue: 0.9 g of an orange-coloured oil, which is employed without further purification in the following synthesis step and has the following structure:

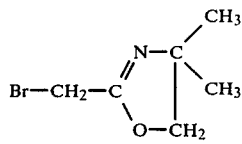

Acemetacin derivative (a) 1.43 g (0.004 mol) of 1-(4-chlorobenzoyl)-5-methoxy-2-methylindole-3-acetic acid are dissolved in 20 ml of absolute dimethylformamide, and, after the addition of 0.28 g (0.002 mol) of powdered potassium carbonate under a protective atmosphere of N$_2$, in the absence of moisture and while stirring, are converted into the potassium salt after 1.5 hours at 40° C. Thereafter, 0.77 g (0.004 mol) of 4,4-dimethyl-2-oxazolin-2-yl-methyl bromide is added, and the reaction is carried out for 5.5 hours at 60° to 70° C. (pH: 6 to 7).

The residue obtained after distilling off dimethylformamide at 40° C. in the vacuum from a water-jet pump is dissolved in ethyl acetate, the solution is extracted twice by shaking with potassium bicarbonate solution, dried (Na$_2$SO$_4$), and filtered, and the solvent is evaporated off.

Residue: 1.4 g of brown oil.

(b) Preparation of

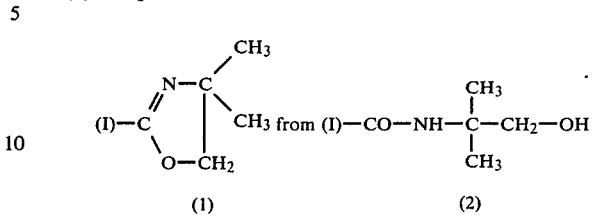

9.74 g (0.02 mol) of (2) are dissolved in 20 ml of o-dichlorobenzene, and the solution is heated under reflux (185° C.) for 5 hours, while stirring, in the absence of moisture (CaCl$_2$ tube) and under a protective atmosphere of N$_2$. The solvent is distilled off at 45° C. and $5.10^{31}$ $^2$ mm Hg in a rotary evaporator, and the pale brown oily residue (=9.2 g) is subjected to high-vacuum distillation in a bulb tube.

Yield: 6.5 g of (1)=69.3% of theory; b.p.: 194 to 206° C./$4.10^{-4}$ mm Hg, yellow oil which crystallises after trituration and while cooling; m.p: 51° to 53° C. The hydrochloride has a melting point of 266° to 270° C.

Preparation of acemetacin

Splitting off the protective group in

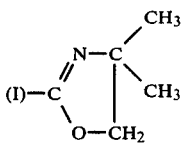

All attempts to split off the protective group led primarily to opening of the oxazole ring, with the formation of the intermediate product

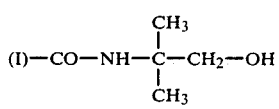

This is subjected, as described in Example 4, to amide cleavage in the side chain by means of dinitrogen tetroxide, acemetacin being formed.

We claim:
1. An indole compound of the formula (I)

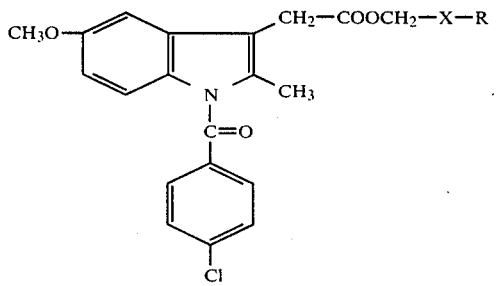

in which
X represents —COO— or —CONH— and
R represents a tetrahydrofuran-2-yl- or a tetrahydropyran-2-yl- group, and their pharmaceutically acceptable salts.

2. an indole compound of claim 1, in which

X represents —COO— and

R represents

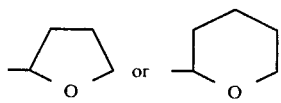

3. An indole compound of claim 2 in which R represents

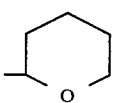

4. A pharmaceutical composition comprising an antiphlogistically effective amount of a compound of claim 1 in admixture with an inert pharmaceutically suitable excipient.

5. A pharmaceutical composition of claim 4 in the form of a sterile or physiologically isotonic aqueous solution.

6. A pharmaceutical composition of claim 4 in the form of tablets, pills, dragees, capsules, ampules, suppositories or gels.

* * * * *